United States Patent [19]

Peiler et al.

[11] Patent Number: 5,273,521
[45] Date of Patent: Dec. 28, 1993

[54] TAMPON APPLICATOR FOR DELIVERY OF A MEDICAMENT

[76] Inventors: Frances K. Peiler, 45-850 #G1 Luana Pl., Kaneohe, Hi. 96744; Larisa H. Peiler, 505 Kailua Rd., Kailua, Hi. 96734

[21] Appl. No.: 936,101
[22] Filed: Aug. 26, 1992
[51] Int. Cl.⁵ .................. A61F 13/32; A61F 13/34
[52] U.S. Cl. .......................... 604/13; 604/15; 604/904
[58] Field of Search .................. 604/11–18, 604/285, 286, 904

[56] References Cited

U.S. PATENT DOCUMENTS

| | | | |
|---|---|---|---|
| 3,102,540 | 9/1963 | Bentov | 604/11 X |
| 3,559,646 | 2/1971 | Mullan | 604/15 |
| 3,884,233 | 5/1975 | Summey | 604/15 |
| 3,913,572 | 10/1975 | Wheeler | 604/15 X |
| 4,405,323 | 9/1983 | Auerbach | 604/285 |
| 4,421,504 | 12/1983 | Kline | 604/12 |
| 4,857,044 | 8/1989 | Lennon | 604/904 X |

Primary Examiner—Randall L. Green
Assistant Examiner—Mary Beth Jones

[57] ABSTRACT

A tampon assembly adapted carrying a for medicament for selective expulsion during use has a tubular inserter, closed at one end, on which an elongated tampon body is mounted by means of a longitudinal bore extending through the body so as to slidably engage the exterior of the inserter at the closed end. A medicament disposed in the remainder of the bore is expelled from the bore by longitudinal relative movement between the inserter and the tampon body along the bore. The tampon body is comprised of an absorbent material so as to have a porous outer surface formed in the shape of radially-disposed longitudinal pleats and porous inner surface formed by the bore, between which a plurality of perforations extend, with string means attached to the tampon body for use in its removal after use.

6 Claims, 1 Drawing Sheet

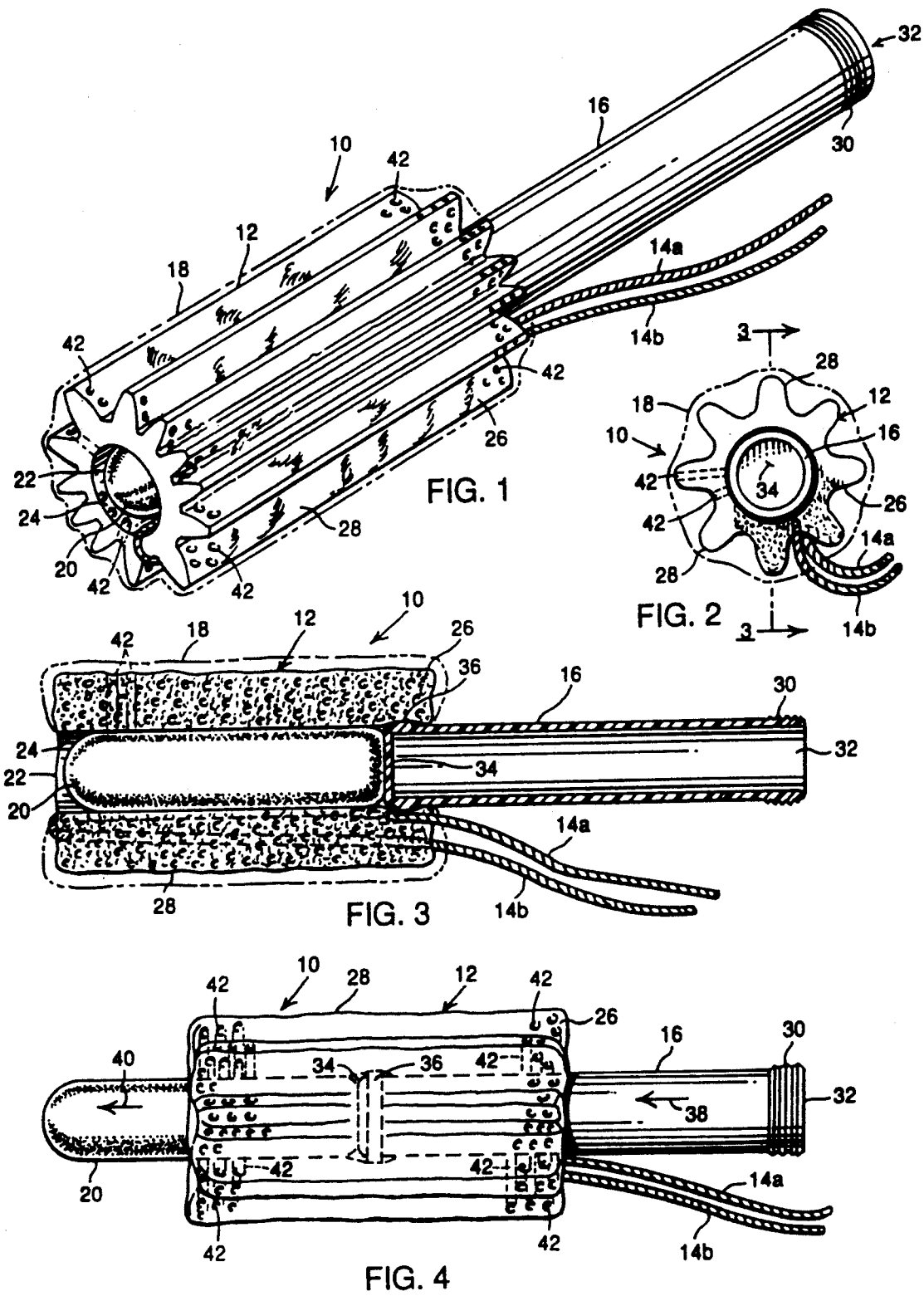

TAMPON APPLICATOR FOR DELIVERY OF A MEDICAMENT

BACKGROUND OF THE INVENTION

I. Field of the Invention

The present invention relates to tampons, and more particularly, to a tampon adapted to carry a medicament into the vaginal cavity where it is expelled from the tampon prior to activation.

II. Description of the Prior Art

Tampons utilized to carry medication or other materials into the vaginal cavity are well known, and are illustrated, for example, in U.S. Pat. No. 4,309,997, issued Jan. 12, 1982; and U.S Pat. No. 4,318,405, and various other patents described therein. All tampons have in common the use of an absorbent material, generally referred to as hydrophilic. In addition to the aforementioned patents, hydrophilic materials are described in, inter alia, U.S. Pat. No. 4,475,911, issued Oct. 9, 1984 As used herein, the term "absorbent" refers to materials which are hydrophilic as that term used in U.S. Pat. No. 4,475,911.

As the foregoing patents demonstrate, it is well known to use various "medicaments," which, as used herein, includes materials such as deodorants and the like as well as material whose use is more generally considered to be for therapeutic purposes. Medicaments may be used seriatim in conjunction with tampons, that is, the medicament is inserted into the vaginal cavity, followed by the insertion of a tampon to prevent leakage. Such a seriatim procedure has numerous obvious disadvantages. Attempts to avoid these disadvantages generally fall into two categories, either the tampon is impregnated with the medicament, such as is described in U.S. Pat. No. 4,309,997, or the medicament is carried in encapsulated form by the tampon, as is described in U.S. Pat. No. 4,318,405. Devices of the type described in U.S. Pat. No. 4,309,997 present problems related to the shelf life of the medicament, allergic reactions to the type of medicament used, and the inconvenience of pre-wetting the tampon, which is often required. Tampons of the type described in U.S. Pat. No. 4,318,405 retain the encapsulated medicament in the tampon both before and after insertion of the tampon into the vaginal cavity, and so may suffer from many of the same disadvantages as the impregnated tampons. In addition, upon dissolving of the encapsulated medicament, much of the medicament will be absorbed by the tampon itself, rather than being applied directly to the body surfaces. Because of the relatively small volume of medicament carried in such a device, often the medicament fails to reach the affected area in sufficient strength. There is also a possibility that the vaginal cavity may be lacking in a sufficient amount of body fluid to dissolve the capsule and ensure medicament application.

SUMMARY OF THE PRESENT INVENTION

According to the present invention, a tampon assembly adapted for carrying a medicament for selective expulsion during use has a tubular inserter, closed at one end, on which an elongated tampon body is mounted by means of an axial bore extending through the body so as to slidably engage the exterior of the inserter at the closed end, the tampon body being is comprised of an absorbent material so as to have a porous outer surface formed in the shape of radially-disposed longitudinal pleats and a porous inner surface formed by the bore, with string means attached to the body portion for use in removing the tampon body after use. A medicament, preferably in a solid, gelatin, ointment, foam, paste or encapsulated form, is disposed in the remainder of the bore so as to abut the inserter closed end, and is selectively expelled from the bore by longitudinal relative movement between the inserter and the tampon body portion along the bore. In the preferred embodiment, a peripheral ring is formed on the inserter adjacent the closed end so as to engage the tampon body portion within the bore to insure expulsion of the medicament as the peripheral ring moves down the bore.

DESCRIPTION OF THE DRAWING

The present invention may be more readily understood by referring to the accompanying drawing, in which:

FIG. 1 is a perspective view of a tampon assembly according to the present invention;

FIG. 2 is a right side elevational view of the tampon assembly shown in FIG. 1;

FIG. 3 is a view, in section, taken along lines 3—3 of FIG. 2; and

FIG. 4 is a plan view of the tampon assembly of FIG. 1 illustrating the ejection of a medicament from the tampon assembly.

DETAILED DESCRIPTION OF THE PREFERRED EMBODIMENT

Referring now to FIGS. 1 through 3, there is shown a tampon assembly 10 according to the present invention, which consists of a tampon body 12, a withdrawal string 14a, 14b, and a wand or inserter 16. Preferably, the tampon body 12 is enclosed in a removable protective covering, 18, shown in dotted lines in FIGS. 1 through 3, to maintain the cleanliness of the tampon body 12 prior to use. A medicament 20 is disposed in a longitudinal bore 22 extending through the tampon body 12. The withdrawal string 14 is illustrated as being configured in a "U", so that one end 14a extends through the bore 22 and the other end 14b extends along the external surface of the tampon body portion 12.

The tampon body 12 is formed of an absorbent material, as that term has been previously defined, so that the bore 22 forms a porous interior surface 24. The tampon body 12 has a porous outer surface 26 in the form of a series of longitudinally aligned, see FIG. 1, and radially-extending, circumferentially-disposed pleats (see FIG. 2).

The wand or inserter 16 has a grip 30 formed at one end thereof. As is shown in FIG. 3, the wand 30 has an open end 32 adjacent the grip 30 and a closed end 34, which abuts the encapsulated medicament 20. A peripheral ring 36 is formed on the wand 16 adjacent the closed end 34 so as to directly engage the porous inner surface 24 of the tampon body portion 16 at the bore 22 to scrape the interior of the bore 22 as the medicament 20 is ejected from the tampon body 12, as will be described hereinafter, in addition to providing a seal of the bore 22 until final withdrawal of the wand 16 from the tampon body portion 12.

Referring now to FIG. 4, the tampon assembly 10 is shown in a disposition in which the medicament 20 is in the process of being expelled from the tampon body 12. For purposes of ease of understanding of the operation of the tampon assembly 10, the insertion of the tampon assembly 10 into the vaginal cavity has not been shown.

Such insertion is performed in the conventional manner. Specifically, the process would include the removal of the removable protective covering 18 from the tampon body portion, the insertion of the medicament 20 into the bore 22 if not already inserted, the insertion of the wand 16 into the bore 22 either prior to or subsequent to the insertion of the medicament thereunto, and the insertion of the tampon assembly, so assembled, into the vaginal cavity with the ends of the withdrawal string 14 remaining outside the vaginal cavity. As is indicated by the arrow 38, the wand 16 is moved so that the closed end 34 passes along the bore 22, thus moving the medicament 20 out of the bore 22, as is indicated by the arrow 40. At such time as the medicament 20 is completely expelled from the bore 22, the movement of the wand 16 in the direction shown by the arrow 38 is terminated, and the wand then moved in the opposite direction to the movement shown by the arrow 38, until the wand is completely withdrawn from the tampon body and is then further withdrawn from the vaginal cavity. Thus, upon expulsion of the medicament 20 from the tampon body 12 as above described, and the withdrawal of the wand 16 from the tampon body 12 and the vaginal cavity, the medicament 20 is dissolved within the vaginal cavity while the tampon body 12 functions as a normal tampon to absorb body fluids in the vaginal cavity as well as seal the vaginal cavity to maintain the medicament therewithin.

In the preferred embodiment, the tampon body 12 has a plurality of randomly-disposed perforations 42 extending between the outer surface 26 and the bore 20 along the length thereof. In FIGS. 1 and 4, only the perforations 42 adjacent the ends of the tampon body are illustrated, it being understood that the use of the perforations 42 is not limited to only those locations illustrated in FIGS. 1 and 4, but preferably extend along the length of the tampon body 112. The use of the perforations 42 is particularly preferred when it is desirable to have the medicament 20 be absorbed into the tampon body 12 after expulsion therefrom, so as to act in a manner similar to an internal bandage in applying the medicament within the vaginal cavity.

In the preferred embodiment shown, the wand 16 utilizes the peripheral ring 36 in order to compress that portion of the porous interior surface 24 of the tampon body 12 as the ring 36 moves along the bore 22. If desired, in order to avoid the peripheral ring 36 passing out of the bore 22 at the time the medicament 20 is expelled therefrom, with the possibility that the ring 36 would not then be readily withdrawable into the bore 22 to permit the withdrawal of the wand 16 from the tampon body 12, the length of the withdrawal string 14 may be adjusted to provide a guidance to the user as to the proper length of movement of the wand 16 into the bore 22. The string 14 may also be held by the user during the movement of the wand 16 through the bore 22 in order to assist in the initiation and continuation of the relative movement of the wand 16 with respect to the tampon body 12 as indicated by the arrow 38. Various other methods are utilizable, if so desired, in order to avoid the passage of the peripheral ring 36 out of the bore 22 at the time of expulsion of the medicament 20 therefrom. For example, a flange could be formed on the wand 16 at the appropriate longitudinal point so as to engage the tampon body 12 to terminate relative movement between the wand 16 and the tampon body 12 at the point of expulsion of the medicament 20 from the bore 22.

From the foregoing description, it will be apparent that the present invention may be distributed in any one of at least three forms. For example, the tampon assembly 10 may be distributed as shown in FIG. 1, with the medicament already inserted. Alternatively, the tampon body 12 and wand 16 may be distributed without the medicament, which then is inserted in the bore 22 by the user immediately prior to use, thereby avoiding a shelf-life problem with respect to the medicament. In addition, the tampon body 12 may be packaged separately from the wand 16, since the wand 16 may be reused. In such an embodiment, a number of tampon bodies 12 may be used over a period of time with a single wand 16, thereby reducing both the cost to the user and the shipping weight and storage volume required.

The present invention relates to the structures described above and hereinafter claimed with respect to the tampon assembly 10 and the components thereof, and not to any particular materials of construction. The term absorbent, as used herein, as stated above, comprehends the use of any appropriate hydrophilic material. The wand 16 may be made of any appropriate material, such as a nontoxic lightweight moldable plastic. While it is tubular in the preferred embodiment for purposes of economy of weight and material, the wand 16 may be solid if desired or may consist, for example, of a rod with an expanded head functioning as the equivalent of the closed end 34. The material of the string is conventional, and therefore the term "string," and the other terms used herein, unless otherwise defined herein, are not limited to the precise materials or depictions contained herein, but rather include structures and materials within the permissible range of equivalents thereto. The removable protective covering 18 is also of conventional material, such as paper or plastic film. The cover 18 may completely enclose the entire tampon assembly 10, as when the medicament 20 is included in the device as distributed. Obviously, the tampon body 12 and medicament 20 can be packaged separately from the wand 16, or the tampon body 12 and wand 16 can be packaged separately from the medicament 20, or the tampon body 12 can be packaged separately from the medicament 20 and the wand 16. Consequently, in FIGS. 1 through 3, the tampon body 12 is shown as enclosed by the protective covering 18 for purposes of illustration only, and not as a limitation.

The invention claimed is:

1. A tampon assembly comprising:
   a tubular inserter having a closed end;
   a generally cylindrical tampon body slidably disposed on said inserter by means of a longitudinal bore formed in the tampon body so as to enclose said tubular inserter closed end, said tampon body being comprised of an absorbent material having an outer surface which is formed in a circular array of porous longitudinal pleats and with a porous internal surface formed by said bore, and in which said closed end of said inserter is normally disposed within the tampon body bore adjacent a first end of the tampon body so as to leave the remainder of the bore open;
   a medicament disposed within the remainder of the bore so as to abut the closed end of the inserter; and
   string means connected to said tampon body and operable to assist in the withdrawal of the tampon after use.

2. A tampon assembly according to claim 1, and in which the tubular inserter has an external ring formed thereon adjacent said closed end so as to engage the tampon body within the bore.

3. A tampon assembly according to either claim 1 or claim 2, and in which the tampon body has a plurality of perforations extending therethrough between the outer surface and the internal surface.

4. A tampon assembly adapted for utilization with a medicament comprising:

a wand having at least one closed end;

an elongated tampon body having a first end and a second end and a longitudinal bore extending therebetween, said wand closed end being disposed within said bore adjacent said tampon body first end so that the tampon body bore is engaged by the wand closed end to close said bore at said tampon body first end, the tampon body bore being normally open at the second end thereof for receiving the medicament, whereby relative movement of the wand closed end toward the tampon body second end is operable to move the medicament along the tampon body bore and out the tampon body second end, said tampon body being formed of an absorbent material so as to have a porous internal surface defined by said bore and having a porous peripheral surface formed by a series of radially-disposed longitudinal pleats of said absorbent material; and string means engaging said tampon body and operable to assist in the withdrawal of the tampon body after use.

5. A tampon assembly according to claim 4, and in which the wand has an external ring formed thereon adjacent said closed end so as to engage the tampon body within the bore.

6. A tampon assembly according to either claim 4 or claim 5, and in which the elongated tampon body has a plurality of perforations extending therethrough between the peripheral surface and the internal surface.

* * * * *